(12) United States Patent
Koyama et al.

(10) Patent No.: US 8,790,907 B2
(45) Date of Patent: *Jul. 29, 2014

(54) METHOD FOR DETACHMENT AND PREPARATION OF LIVING MICROORGANISMS

(75) Inventors: Sumihiro Koyama, Yokosuka (JP);
Tadashi Maruyama, Yokosuka (JP);
Chiaki Kato, Yokosuka (JP); Yuichi Nogi, Yokosuka (JP); Yuji Hatada, Yokosuka (JP); Yukari Ohta, Yokosuka (JP); Masaaki Konishi, Yokosuka (JP); Taishi Tsubouchi, Yokosuka (JP)

(73) Assignee: Japan Agency for Marine-Earth Science and Technology, Yokosuka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/359,797

(22) Filed: Jan. 27, 2012

(65) Prior Publication Data

US 2013/0196404 A1 Aug. 1, 2013

(51) Int. Cl.
*C12N 1/00* (2006.01)
*C12N 1/04* (2006.01)
*C12N 11/14* (2006.01)

(52) U.S. Cl.
USPC ............................ 435/243; 435/260; 435/176

(58) Field of Classification Search
USPC .................................................. 435/243, 260
See application file for complete search history.

(56) References Cited

U.S. PATENT DOCUMENTS

| 5,126,024 | A | 6/1992 | Bonelli et al. |
| 8,071,319 | B2 * | 12/2011 | Metzger et al. ................ 435/7.2 |
| 2006/0134704 | A1 | 6/2006 | Muraguchi et al. |
| 2009/0181859 | A1 | 7/2009 | Muraguchi et al. |
| 2011/0287504 | A1 * | 11/2011 | Mets .............................. 435/167 |
| 2012/0264186 | A1 * | 10/2012 | Koyama ...................... 435/173.1 |

FOREIGN PATENT DOCUMENTS

| JP | 10-042857 | * | 2/1998 |
| JP | 10-0428547 | | 2/1998 |
| JP | 2001-161359 | | 6/2001 |
| JP | 2004-173681 | | 6/2004 |
| JP | 2005-312343 | | 11/2005 |
| JP | 2008-295382 | | 12/2008 |
| WO | WO 2010/072257 | | 7/2010 |
| WO | WO 2011052717 | A1 * | 5/2011 |

OTHER PUBLICATIONS

Sigma D8537 Dulbecco's Phosphate Buffered Saline Nov. 20, 2008 [retrieved on Oct. 26, 2012] Retrieved from the Internet <http://web.archive.org/web/20081120045507/http://www.sigmaaldrich.com/catalog/search/ProductDetail/SIGMA/D8537>.*

(Continued)

*Primary Examiner* — Jon P Weber
*Assistant Examiner* — Kara Johnson
(74) *Attorney, Agent, or Firm* — Ditthavong & Steiner, P.C.

(57) ABSTRACT

A method for immobilizing living microorganisms includes a step (1) of disposing a solution containing microorganisms as an electrolyte on the surface of a substrate at least one portion of which is an electrode, and applying a constant potential to the electrode to cause at least a portion of the microorganisms to attach to the surface of the substrate. The constant potential in step (1) is greater than −0.5 V but not greater than −0.2 V (vs Ag/AgCl) or greater than +0.2 V but not greater than +0.4 V (vs Ag/AgCl). The electrolyte in step (1) does not contain a source of nutrition for the microorganisms.

9 Claims, 10 Drawing Sheets

(56) References Cited

OTHER PUBLICATIONS

Sigma Product Information Nov. 20, 2008 [retrieved on Oct. 26, 2012] Retrieved from the Internet <http://web.archive.org/web/20070306043616/http://www.sigmaaldrich.com/sigma/formulation/d8537for.pdf>, hereinafter Sigma Product Info.*

Gregory et al., Graphite electrodes as electron donors for anaerobic respiration. Environmental Microbiology, vol. 6 No. 6 (2004) pp. 596-604.*

Manome et al., "Application of gel microdroplet and flow cytometry techniques to selective enrichment of non-growing bacterial cells", FEMS Microbiology Letters, 2001, pp. 29-33, 197, Elsevier Science B.V.

Extended European Search Report for corresponding EP Application No. 12002019.3-2405, Sep. 21, 2012.

Poortinga Albert T et al., "Controlled electrophoretic deposition of bacteria to surfaces for the design of biofilms", Biotechnology and Bioengineering, vol. 67, No. 1, Jan. 5, 2000, pp. 117-120, XP002683069.

Hong Seok Hoon et al., "Effect of electric currents on bacterial detachment and inactivation", Biotechnology and Bioengineering, vol. 100, No. 2, Jun. 2008, pp. 379-386, XP002683070.

Van Der Borden A J et al., "Electric block current induced detachment from surgical stainless steel and decreased viability of *Staphylococcus epidermidis*", Biomaterials, Elsevier Science Publishers BV., Barking, GB, vol. 26, No. 33, Nov. 1, 2005, pp. 6731-6735, XP027767641.

Neirinck B et al., "Electrophoretic deposition of bacterial cells", Electrochemistry Communications, Elsevier, Amsterdam, NL, vol. 11, No. 9, Sep. 1, 2009, pp. 1842-1845, XP026716416.

Longton R W et al., "Isoelectric focusing of bacteria: Species location within an isoelectric focusing column by surface charge", Archives of Oral Biology, Pergamon Press, Oxford, GB, vol. 20, No. 2, Feb. 1, 1975, pp. 103-106, XP026182304.

* cited by examiner

50μg SOIL SAMPLE

ATTACHMENT

-0.4-V VS. Ag/AgCl FOR 24h IN 280mM MANNITOL

ITO ELECTRODE    GLASS

100 μm

DIFFERENTIAL INTERFERENCE     BACLIGHT STAINING     SUPERIMPOSE DISPLAY

ALMOST SAME ATTACHMENT RATES COMPARED TO THE OPEN CIRCUIT

DETACHMENT

±1.0-V, 3-MHz RECTANGULAR WAVE POTENTIAL APPLICATION

-0.4-V VS. Ag/AgCl FOR 24h IN PBS(-) → ±1.0-V VS. Ag/AgCl FOR 1h IN 280mM MANNITOL

DIFFERENTIAL INTERFERENCE     BACLIGHT STAINING     SUPERIMPOSE DISPLAY

SURVIVAL RATES AFTER TRIANGULAR WAVE POTENTIAL APPLICATION : 13%

DETACHMENT RATES FROM THE ELECTRODE : 62%

FIG. 9

METHOD FOR DETACHMENT AND PREPARATION OF LIVING MICROORGANISMS

TECHNICAL FIELD

The present invention relates to a method for immobilizing living microorganisms utilizing constant potential electrolysis, and to a method for preparing living microorganisms utilizing this method.

BACKGROUND ART

The capture and immobilization of microorganisms on a carrier is known (Patent Reference 1). The invention described in Patent Reference 1 is a method of rapidly preparing a film of microorganisms of any area and any shape on a carrier, in which the species of the microorganism forming the biofilm is controlled.

The biofilm method employed in waste water treatment is a purification method employing the pollutant decomposing action of a group of micro-organisms attaching in the form of a film to a carrier. At the start of operation of the biofilm method, it is necessary to cause the biofilm to attach to the carrier. Conventionally, however, the carrier is immersed in active sludge or a microorganism broth, and attachment of the organism requires waiting for the organism to naturally attach to the carrier. That makes it difficult to control the attachment area, attachment shape, or species of attaching microorganism. Based on the description of Patent Reference 1, the invention described in Patent Reference 1 was provided with the object of eliminating this problem.

The invention (claim 1) described in Patent Reference 1 is a method of preparing a microorganism film, characterized by: positioning in a liquid containing a microorganism a substrate on which is provided an electrode capable of generating a nonuniform electric field, applying an ac voltage to the electrode to generate a nonuniform electric field in the liquid, and rendering the permittivity of the cells of a specific microorganism greater than the permittivity of the medium to selectively cause the specific microorganism to attach to the substrate.

Attempts have been made to specify, select, and use selected cells at the single-cell level. For example, the individual detection of the antigen specificity of single lymphocytes, the retrieval of a single antigen-specific lymphocyte that has been detected, and the use of the single antigen-specific lymphocyte that has been retrieved to, for example, produce an antibody has been examined (Patent Reference 2). In Patent Reference 2, a microwell array chip is used to detect antigen-specific lymphocytes. Within the microwell array chip, the shape and dimensions of each microwell are configured so as to allow only a single lymphocyte to be contained in each microwell.

When animal cells are cultured on a substrate surface, an adhesive protein known as extracellular matrix is known to form outside the cells, attaching the cells to the substrate surface. The detachment and use of cells thus attached to the substrate surface is known. The use of an electrical stimulus as the method of detachment is known (Patent References 3 to 5).

[Patent Reference 1] Japanese Unexamined Patent Publication (KOKAI) No. 2001-161359
[Patent Reference 2] Japanese Unexamined Patent Publication (KOKAI) No. 2004-173681
[Patent Reference 3] Japanese Unexamined Patent Publication (KOKAI) No. 2008-295382
[Patent Reference 4] Japanese Unexamined Patent Publication (KOKAI) No. 2005-312343
[Patent Reference 5] Japanese Unexamined Patent Publication (KOKAI) Heisei No. 10-42857
[Nonpatent Reference 1] Manome et al., FEMS Microbiol. Lett. 197, 29-33 (2001)

SUMMARY OF THE INVENTION

Thus far, no attempt has been made to specify, select, and use the selected microorganism in a viable condition at the single cell or small cell group level. The method described in Patent Reference 1 is a method of preparing a microorganism film, but not a method of immobilizing and specifying a microorganism at the single cell level or small cell group level. Nor does Patent Reference 1 describe detaching (de-immobilizing) in a viable condition the microorganisms that have been immobilized. Nor do Patent References 3 to 5 contain any description of the detachment of microorganisms.

Conventionally, due to the lack of a technique for controlling the placement of the microorganisms at specific positions on the substrate, techniques based on cell sorters have been the mainstream in the small-scale analysis of microorganisms (Nonpatent Reference 1).

However, in the analysis of microorganisms with a cell sorter, multiple microorganisms absorb firmly to soil microparticles, making it extremely difficult to directly analyze the microorganisms living in soil at the single-cell level.

The present invention has for its object to provide a new means of immobilizing and positioning microorganisms in a viable condition on a substrate surface at the single-cell level or in small groups, and to provide a means of using this new means to detach (release) in a viable condition the microorganisms that have been immobilized.

The present inventors discovered that it was possible to employ an electrolyte in the form of a buffer not containing a nutrition source and in which living microorganisms (prokaryotes) had been dispersed, and to apply a weak potential that did not produce an electrochemical reaction to cause living microorganisms to attach to the cathode substrate. They further discovered that microorganisms (prokaryotes) that had been attached to the electrode substrate by this method could be subjected to a high frequency wave potential to quantitatively release and retrieve them in a viable condition from the electrode surface with almost no damage. The present invention was devised based on this knowledge.

The present invention is as set forth below:

[1]
A method for immobilizing living microorganisms comprising a step (1) of disposing a solution containing microorganisms as an electrolyte on the surface of a substrate at least one portion of which is an electrode, and applying a constant potential to the electrode to cause at least a portion of the microorganisms to attach to the surface of the substrate, characterized in that:
the constant potential in step (1) is greater than −0.5 V but not greater than −0.2 V (vs Ag/AgCl) or greater than +0.2 V but not greater than +0.4 V (vs Ag/AgCl); and
the electrolyte in step (1) does not contain a source of nutrition for the microorganisms.
[2]
A method for preparing living microorganisms, comprising a step (1) of disposing a solution containing microorganisms as an electrolyte on the surface of a substrate at least one portion of which is an electrode, applying a constant potential to the electrode to cause at least a portion of the microorganisms to attach to the surface of the substrate and a step (2) of applying a high-frequency wave potential to the electrode to detach in a viable condition the microorganisms that have been attached to the surface of the substrate; characterized in that:

the constant potential in step (1) is greater than −0.5 V but not greater than −0.2 V (vs Ag/AgCl) or greater than +0.2 V but not greater than +0.4 V (vs Ag/AgCl);

the high-frequency wave potential in step (2) has a frequency falling within a range of 1 KHz to 10 MHz and a potential range of ±1.0 V (vs Ag/AgCl) or narrower;

the electrolyte in step (1) does not contain a source of nutrition for the microorganisms; and the electrolyte of step (2) has a salt concentration of 10 g/L or lower.

[3]
The method according to [1] or [2], wherein the electrolyte in step (1) has a salt concentration of 10 g/L or lower.

[4]
The method according to [1] or [2], wherein the electrolyte in steps (1) and (2) is a $Ca^{2+}$ and $Mg^{2+}$-free phosphate buffer solution.

[5]
The method according to [1] or [2], wherein the electrolyte in step (1) is artificial seawater or natural seawater, and the constant potential in step (1) is greater than −0.4 V but not greater than −0.2 V (vs Ag/AgCl) or greater than +0.2 V but not greater than +0.4 V (vs Ag/AgCl).

[6]
The method according to any one of [2] to [5], wherein the high-frequency wave potential is a rectangular wave, sine wave, or triangle wave.

[7]
The method according to any one of [1] to [6], wherein the entire surface of the substrate is an electrode.

[8]
The preparation method according to any one of [2] to [7], wherein a portion of the surface of the substrate is an electrode, and the microorganisms on the electrode surface and on the non-electrode surface in the vicinity of the electrode in step (2) are detached in a viable condition.

[9]
The preparation method according to any one of [2] to [8], comprising the step of further cultivating the microorganisms that have been detached to cause the microorganism to proliferate.

The present invention makes it possible to cause a microorganism (prokaryote) to attach to the surface of an electrode in a viable condition. The present invention further makes it possible to retrieve in a viable condition the microorganism that has been caused to attach to the surface of the electrode. These methods can be employed on Gram-negative bacteria in the form of *Escherichia coli* (*E. coli*) and on Gram-positive bacteria in the form of *Bacillus subtilis* (*B. subtilis*).

The present invention also permits the comparative analysis in microorganisms of gene and protein expression between single cells by high-performance optical microscopy, such as a confocal laser microscopy, in the manner of single-cell analysis that is conducted on animal cells, by attracting and attaching various microorganisms in soil onto an electrode substrate. It also makes it possible to retrieve the microorganism following analysis.

The method of the present invention makes it possible to electrically remove multi-drug resistant bacteria contaminating blood products and the like, and to remove microorganisms present in water, such as in bath water.

MODES OF CARRYING OUT THE INVENTION

<Method for Immobilizing Living Microorganisms>

The first aspect of the present invention relates to a method for immobilizing living microorganisms.

This method comprises a step (1) of disposing a solution containing microorganisms as an electrolyte on the surface of a substrate at least one portion of which is an electrode, and applying a constant potential to the electrode to cause at least a portion of the microorganisms to attach to the surface of the substrate. It is characterized in that: the constant potential in step (1) is greater than −0.5 V but not greater than −0.2 V (vs Ag/AgCl) or greater than +0.2 V but not greater than +0.4 V (vs Ag/AgCl); and the electrolyte in step (1) does not contain a source of nutrition (medium) for the microorganisms.

Step (1)

Step (1) is a step of applying a constant potential to the surface of a substrate at least one portion of which is an electrode. The substrate at least one portion of which is an electrode is not specifically limited. The entire surface of the substrate can constitute an electrode, or some portion thereof can constitute an electrode and some other portion can be a non-electrode (substrate). On the substrate at least one portion of which is an electrode, for example, an electrode layer can be provided on a substrate that is not an electrode, or the entire member can be an electrode, such as a carbon electrode. When an electrode layer is provided on a substrate that is not an electrode, the electrode can be present on part or all of the surface of an insulating substrate, A substrate on which such an electrode is present can be, for example, obtained by coating indium [tin] oxide (ITO) on a glass slide. However, the insulating substrate is not limited to a glass slide, and is not specifically limited other than that it be a non-electrically conductive solid. It can be comprised of a non-electrically conductive organic or inorganic material. Examples of non-electrically conductive organic and inorganic materials, in addition to glass, are plastics and ceramics. The electrode is not limited to indium [tin] oxide (ITO); an electrode of any known electrode material can be suitably employed.

When an electrode layer is provided on a substrate, the electrode layer can be provided over the entire surface of the substrate, or the electrode layer can be provided over a portion of the surface of the electrode substrate. When an electrode layer is provided over a portion of the surface of an electrode substrate, the electrode layer can be, for example, in the form of an array or stripes. The size (area or dimensions) of the electrode layer can be suitably determined For example, the area of the electrode can fall within a range of 1 to 900 cm$^2$.

The term "in the form of an array" means, for example, that the electrode layer is arranged as multiple minute regions disposed in columns or rows. The number of minute regions in the columns or rows is not specifically limited. The type (size) of the microorganism and the like can be suitably determined based on the use objective of the substrate on which the microorganism is disposed in an array. For example, a range of 10 to $10^5$ vertically by 10 to $10^5$ horizontally is possible. However, this range is not a limitation. The shape of the surface of the electrode layer in the form of an array can be rectangular (triangular, square, rectangular, polyhedral, and the like), round, elliptical, or the like, and can be suitably determined. The dimensions of the various electrode surfaces in the form of an array can be such that a single microorganism can attach to a single electrode surface. Since microorganisms come in various dimensions, the dimensions of the electrode surface can be suitably determined based on the dimensions of the microorganisms being made to attach. Further, the dimensions of the various electrode surfaces in the form of an array can be such that two or more microorganisms can attach to one electrode surface. Further, the spacing of the individual electrodes can fall within a range of 25 to 100 μm, for example.

In a striped electrode layer, multiple electrode layers in the form of stripes of equal width can be disposed at uniform or varying spacings, or multiple electrode layers in the form of stripes of various widths can be disposed at uniform or varying spacings. The width of the striped electrode layers and the spacing between the striped electrode layers are not specifically limited, and can each independently fall within a range of 25 to 100 μm.

As will be set forth further below, in step (2), not just the cells on the surface of the electrode, but the cells on the non-electrode surface in the vicinity of the electrode, as well, can be detached. The distance from the electrode of the cells on the non-electrode surface that can be detached depends on the potential and on the frequency of the high-frequency wave potential, but is not greater than 100 μm, for example. Accordingly, in the cases of both the array form and stripe form, a spacing of the electrodes falling within a range of 25 to 100 μm permits the detachment of cells on the non-electrode surface.

The electrode layer in the form of an array or stripes on the substrate surface can be formed by, for example, coating an electrode layer on the surface of a substrate, or by forming a mask for an electrode surface in the form of an array or stripes on the surface of the electrode layer, etching the surface of the electrode layer through the mask, and removing the mask. Alternatively, the electrode surface in the form of an array or stripes can be formed on the surface of the substrate by coating the electrode layer on the surface of the substrate through a mask for an electrode surface in the form of an array or stripes, and removing the mask. The formation of the electrode layer, etching of the surface of the electrode layer, and the like can be suitably implemented by the usual methods.

In step (1), a solution containing the microorganisms is positioned as an electrolyte, a constant potential is applied to the electrode, and the microorganisms are caused to attach to at least a portion of the surface of the substrate. The constant potential in step (1) is greater than −0.5 V but not greater than −0.2 V (vs Ag/AgCl) or greater than +0.2 V but not greater than +0.4 V (vs Ag/AgCl). As is specifically indicated in the Examples, when the constant potential that is applied to the electrode to cause attachment of the microorganisms falls within the above range, the microorganisms in the electrolyte attach specifically to the electrode in a viable condition. When the constant potential applied to the electrode falls outside the above range, the microorganisms either do not attach to the electrode, or they attach to the electrode, but not in a viable condition. The above constant potential has been denoted for an Ag/AgCl reference electrode, but can also be denoted using a reference electrode other than Ag/AgCl. It will be understood that even a constant potential denoted using a reference electrode other than Ag/AgCl that falls within the above range denoted for an Ag/AgCl reference electrode satisfies the conditions of the present invention. When denoted using Ag/AgCl as a reference electrode, −1.06 V is the hydrogen generation potential, and +1.69 V is the oxygen generation potential.

The application period of the constant potential to the electrodes can be suitably determined by taking into account the type of microorganism, the type of electrolyte, the concentration of the microorganism in the electrolyte, the potential being applied, and the like. For example, it can fall within a range of 1 to 48 hours.

The electrolyte in step (1) does not contain a source of nutrition for the microorganisms. Attachment of the microorganisms to the surface of the substrate by the application of the constant potential only occurs when the electrolyte does not contain a source of nutrition for the microorganisms contained in the electrolyte. Although the reason is unclear, the microorganisms do not attach to the electrode when the electrolyte contains a source of nutrition for the microorganisms contained in the electrolyte. The term "source of nutrition for the microorganisms" means a source of nutrition that is essential for cultivation of the microorganism, in the form of some or all of the components of the medium that is normally used to cultivate the microorganism. More specifically, the source of nutrition that is not contained in the electrolyte means, for example, sugars, proteins, amino acids, fatty acids, lipids, nucleic acid, and the like.

The term "does not contain a source of nutrition" does not exclude containing trace amounts of sources of nutrition that essentially do not contribute to the growth of the microorganism. In the course of preparing the electrolyte containing the microorganism from a sample containing the microorganism, mixing the original electrolyte solution with the sample without removing the trace quantities of sources of nutrition contained in the sample causes them to be passed on to the sample. Such an electrolyte containing trace quantities of sources of nutrition that are contained in the electrolyte that is subjected to the application of a potential is defined in the present invention as an electrolyte "that does not contain sources of nutrition." Although the sample containing the microorganisms can be mixed with the original solution of the electrolyte to prepare the electrolyte, it is possible to filter or the like the sample containing the microorganisms to remove the trace quantities of sources of nutrition that are passed on with the sample, and then mix the sample with the original solution of the electrolyte to reduce the quantity of sources of nutrition passed on with the sample.

The concentration of the microorganism in the electrolyte is not specifically limited. For example, when causing the microorganism to attach to the surface of the electrode cell by cell, the concentration of the microorganism in the electrolyte is desirably relatively low. However, since the quantity of microorganism attaching to the electrode varies with the constant potential applied and with the application period of the constant potential, the concentration of the microorganism in the electrolyte is one of a number of variables. The concentration of the microorganism in the electrolyte can be suitably determined taking these factors into consideration.

It is desirable for the salt concentration in the electrolyte in step (1) to be 10 g/L or less from the perspective of causing the microorganism to attach to the electrode in a viable condition. The salt concentration desirably falls within a range of 0 to 10 g/L. Further, it is desirable for the electrolyte in step (1) to be a buffer solution from the perspective of causing the microorganisms to attach to the electrode in a viable condition. It is also desirable for the salt concentration in the buffer solution to be 10 g/L or less. The buffer solution is not specifically limited. For example, a phosphate buffer solution (without $Ca^{2+}$, $Mg^{2+}$) is desirable from the perspective of causing the microorganism to attach to the electrode in a viable condition. In addition to a phosphate buffer solution, it is also possible to employ 3-morpholinopropanesulfonic acid (MOPS), N-[Tris(hydroxymethyl)methyl]glycine (tricine), N-(2-hydroxyethyl)piperazine-N'-(2-ethanesulfonic acid) (HEPES), and the like. However, from the perspective of increasing the rate of attachment of the microorganism to the electrode, a phosphate buffer solution (without $Ca^{2+}$, $Mg^2$) is desirable. The pH of the buffer solution can be suitably selected based on the type of microorganism. For example, it will fall within a range of 5 to 9 for common microorganisms.

The electrolyte in step (1) can be artificial seawater or natural seawater. In these cases, the constant potential in step (1) is desirably greater than −0.4 V but not greater than −0.2 V (vs Ag/AgCl) or greater than +0.2 V but not greater than +0.4 V (vs Ag/AgCl). The salt concentration in the case of artificial seawater or natural seawater is about 40 to 50 g/L. When the salt concentration is high, at a range of −0.5 V to −0.4 V, the survival rate of the microorganism attached to the electrode tends to drop.

In the method of the present invention, the microorganism that can be caused to attach to the surface of the electrode in a viable condition is not specifically limited. As disclosed in the Examples, *E. coli*, which is a Gram-positive bacterium, and *B. subtilis*, which is a Gram-negative bacterium, can be caused to attach to the surface of the electrode in a viable condition. The microorganism that can be caused to attach to the electrode surface in a viable condition is not limited. Examples are *E. coli*, *B. subtilis*, *Bacillus halodurans*, *Shewanella violacea*, *Shewanella oneidensis*, *Shewanella surugensis*, *Kocuria rosea*, *Kocuria 4B*, *Shewanella abyssi*, and *Shewanella kaireitica*.

The present inventors examined the effects of attachment to the electrode substrate by the application of a constant voltage on *B. subtilis*, *Bacillus halodurans*, *Shewanella violacea*, *Kocuria rosea*, and *Shewanella oneidensis*. As a result, they confirmed that *S. violacea* was strongly drawn onto an electrode to which a constant potential of −0.3 V vs. Ag/AgCl was applied in artificial seawater, and the other microorganisms were strongly drawn onto electrodes to which a constant potential of −0.4 V vs. Ag/AgCl was applied in the same phosphate buffer solution (without $Ca^{2+}$, $Mg^{2+}$) as for *E. coli*.

<Method for Preparing Living Microorganisms>

The second aspect of the present invention relates to a method for preparing a live microorganism.

This method comprises a step (1) of disposing a solution containing microorganisms as an electrolyte on the surface of a substrate at least one portion of which is an electrode, applying a constant potential to the electrode to cause at least a portion of the microorganisms to attach to the surface of the substrate and a step (2) of applying a high-frequency wave potential to the electrode to detach in a viable condition the microorganisms that have attached to the surface of the substrate.

Further, it is characterized in that the constant potential in step (1) is greater than −0.5 V but not greater than −0.2 V (vs Ag/AgCl) or greater than +0.2 V but not greater than +0.4 V (vs Ag/AgCl); the high-frequency wave potential in step (2) has a frequency falling within a range of 1 KHz to 10 MHz and has a potential range of ±1.0 V (vs Ag/AgCl) or narrower; the electrolyte in step (1) does not contain a source of nutrition for the microorganisms; and the electrolyte of step (2) has a salt concentration of 10 g/L or lower.

Step (1) in the second aspect is identical to step (1) in the first aspect.

In step (2), a high-frequency wave potential is applied to the electrode to which the microorganisms have been attached in a viable condition in step (1) to detach in a viable condition the microorganisms that have been attached to the surface of the substrate. The microorganisms that have been attached to the electrode and the microorganisms that have attached to a non-electrode surface in the vicinity of the electrode are detached by the application of a high-frequency wave potential. Specifically, the high-frequency wave potential has a frequency falling within a range of 1 KHz to 10 MHz, desirably within a range of 1 to 5 MHz. The potential has, for example, a range of ±1.0 V (vs Ag/AgCl) or narrower, such as ±0.9 V (vs Ag/AgCl) or narrower, or ±0.8 V (vs Ag/AgCl) or narrower. The waveform of the high-frequency wave potential can be, for example, that of a rectangular wave, sine wave, or triangle wave.

The electrolyte in step (2) has a salt concentration of 10 g/L or less. Even when the electrolyte in step (1) is artificial or natural seawater with a salt concentration exceeding 10 g/L, the potential can be adjusted to cause the microorganisms to attach to the surface of the electrode in a viable condition. However, when the salt concentration exceeds 10 g/L in step (2), it has been determined that microorganisms cannot be detached from the surface of the electrode in a viable condition. The electrolytes in steps (1) and (2) can be of identical or different compositions. However, the electrolyte in step (2) has a salt concentration of 10 g/L or less. Further, the electrolyte in step (2), in the same manner as the electrolyte in step (1), does not contain a source of nutrition.

During detachment in the course of applying a high-frequency wave potential, the electrolyte is suitably a buffer solution that does not contain calcium and magnesium. That is because the microorganisms were not able to detach electrically when a high-frequency wave potential was applied to an electrolyte containing calcium or magnesium. During detachment in the course of applying a high-frequency wave potential, the electrolyte can be, for example, a $Ca^{2+}$ and $Mg^{2+}$-free phosphate buffer solution [PBS(−)], a $Ca^{2+}$ and $Mg^{2+}$-free Hank's buffered salt, or the like. Of these, PBS(−) is desirable.

In step (2), not just the microorganisms on the surface of the electrode, but the microorganisms on the non-electrode surface in the vicinity of the electrode, as well, can be detached. The distance from the electrode of the microorganisms that can be detached on the non-electrode surface depends on the potential and frequency of the high-frequency wave potential. However, it can be about 100 μm or less. In the course of applying a high-frequency wave potential, the potential is directly applied to the microorganisms on the electrode and indirectly applied to the microorganisms on the non-electrode surface. Accordingly, there is relatively less stress due to the application of the potential on the microorganisms on the non-electrode surface. Even when damage is inflicted to the microorganisms by the application of the potential (due to the conditions of the high-frequency wave potential), there will tend to be less, or no, damage to the microorganisms on the non-electrode surface. A high-frequency wave potential that inflicts a high degree of damage on the microorganisms when applied will sometimes be used because the microorganisms will sometimes attach strongly and not readily detach. In such cases, an electrode shape or disposition that preferentially detaches the microorganisms on the non-electrode surface and the non-electrode surface can be selected so that detachment of the microorganisms on the non-electrode surface is actively conducted.

Figure 1A:
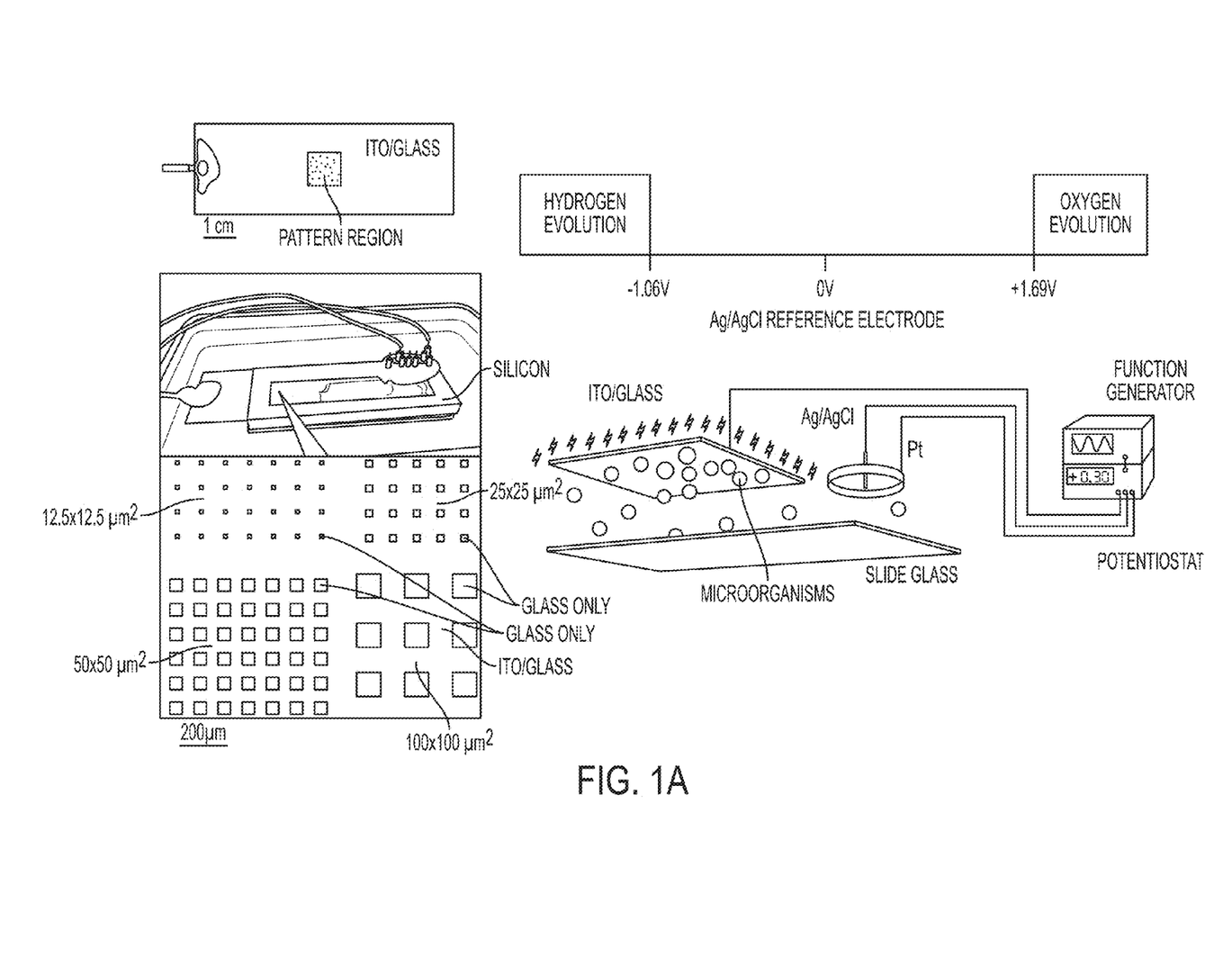
[FIG. 1A] Shows photograph and schematic diagram of electrode chamber.
Figure 1B:
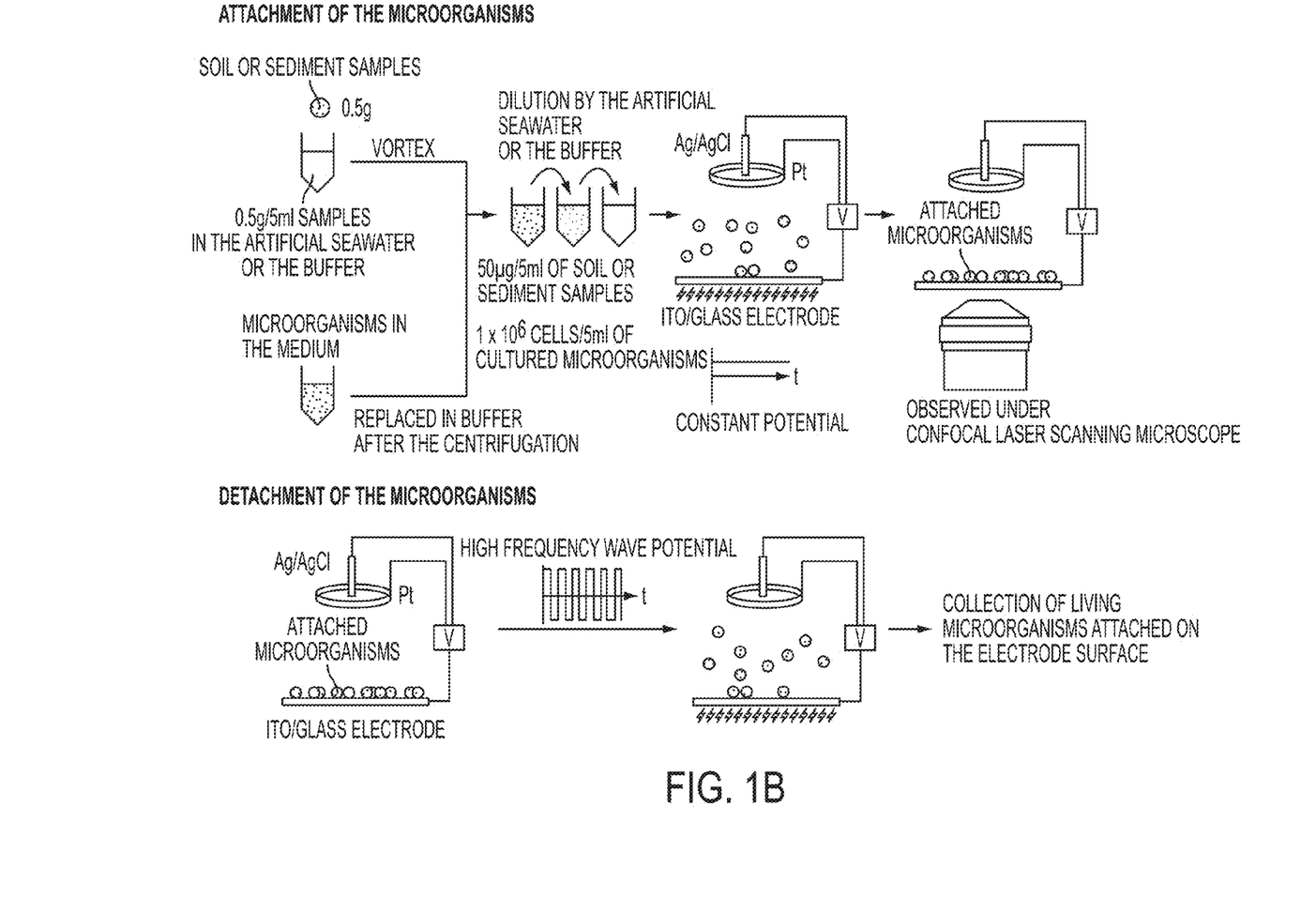
[FIG. 1B] Shows descriptive drawing of attraction and attachment of microorganisms onto electrode and detachment and retrieval therefrom.

In the method of the present invention, as shown in FIG. 1B, microorganisms are caused to attach to the electrode surface of the substrate or the electrode and non-electrode surfaces in step (1). For example, the microorganisms that are caused to attach can be from soil samples, or can be from a culture solution containing microorganisms. The sample containing the microorganisms is suitably diluted with an electrolyte to adjust it to a prescribed concentration, after which a constant potential is applied. As needed, the attachment of the microorganisms to the electrode or non-electrode surface by the application of a constant potential can be observed by confocal microscopy or the like.

In step (2), a high-frequency wave potential is applied to the electrode surface, or to the electrode and non-electrode surfaces, of the substrate to which the microorganisms have attached. That causes the animal microorganisms that have attached to the electrode surface or electrode and non-electrode surfaces to detach in a viable condition.

In the method of the present invention, the survival rate of the microorganisms that have attached to the electrode surface or electrode and non-electrode surfaces of the substrate in step (1) depends on the attachment conditions. By way of example, it falls within a range of 50 to 100 percent. Further, the survival rate of the microorganisms that are detached and retrieved from the electrode surface or electrode and non-electrode surface in step (2) depends on the detachment conditions. By way of example, it falls within a range of 50 to 100 percent.

The method of the present invention can comprise a further step of cultivating the detached microorganisms to cause them to proliferate. The method of cultivating the microorganisms can be suitably adopted based on the type of microorganism.

EXAMPLES

The present invention is described in greater detail below through Examples.

Example 1

In the order indicated below, microorganisms were attached to and detached from ITO electrodes in the 3-electrode chamber shown in FIG. 1A, and a live/dead determination was made (see FIG. 1B).
1) A 0.5 g quantity of soil from a JAMSTEC vegetable garden in which no agricultural chemicals had been employed was added to Dulbecco's PBS(−) (Wako, Osaka, Japan), the overall quantity was adjusted to 5 mL, and the mixture was stirred for 5 minutes with a vortex.
2) The mixture was diluted $10^4$-fold with Dulbecco's PBS(−) and 10 ng/mL soil samples were prepared.
3) To examine whether dead microorganisms would be drawn to the electrode, $10^4$-fold dilution was conducted with 0.02% (w/v) sodium azide (Wako, Osaka, Japan) dissolved in Dulbecco's PBS(−) and 10 ng/mL soil samples were prepared. Alternatively, soil samples that had been processed for one hour with 70% EtOH at 60° C. were employed.
4) The 5 mL soil sample solution was added to a 3-electrode chamber (see FIG. 1A) and a −0.4 V vs. Ag/AgCl potential was applied at room temperature for 24 hours.
5) After applying the potential for 24 hours, the soil sample supernatant was retrieved and the ITO pattern electrode substrate was washed lightly several times with fresh Dulbecco's PBS(−).
6) A 5 mL quantity of fresh Dulbecco's PBS(−) was added to the 3-electrode chamber and a ±1.0 V vs. Ag/AgCl, 3 MHz rectangular wave potential was applied for another one hour at room temperature.
7) Following application of the potential for one hour, the supernatant of the PBS(−) sample was retrieved and the ITO pattern electrode substrate was washed lightly several times with fresh Dulbecco's PBS(−).
8) The living microorganisms having dehydrogenase activity that had attached to the ITO electrodes in 5) were fluorescence stained with Bacstain CTC rapid staining kit for microscopy (Dojindo, Kumamoto, Japan) and then observed by confocal laser microscopy (FV500, Olympus, Tokyo, Japan).
9) The microorganisms that had attached to the ITO electrodes in 5) and 7) were fluorescence stained with Live/dead Baclight bacterial viability kits (Molecular probes, Eugene, Oreg., USA) and a determination was made as to whether they were alive or dead by confocal laser microscopy (FV500).
10) The microorganisms that had been retrieved in the supernatant samples retrieved in 5) and 7) were fluorescence stained with Live/dead Baclight bacterial viability kits and a determination was made as to whether they were alive or dead by confocal laser microscopy (FV500) using a hemacytometer.

Figure 2:
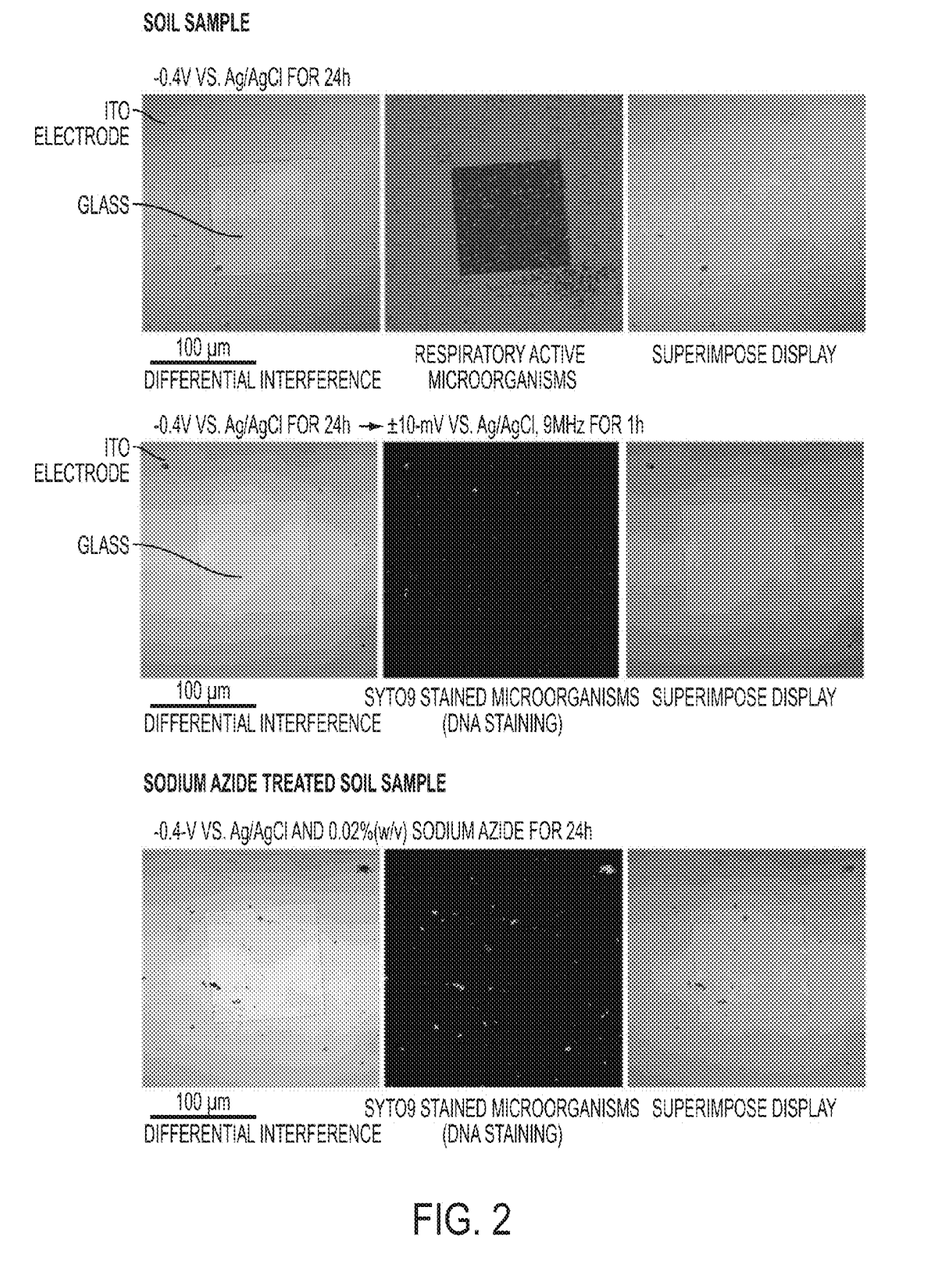
[FIG. 2] Shows result of attracting soil microorganisms onto electrode in Example 1.

The results are given in FIG. 2.

The living microorganisms (prokaryotes) in the soil attached to the electrode substrate to which a weak negative potential had been applied without producing an electrochemical reaction (see the upper portion of FIG. 2). Dead microorganisms did not attach on the surface of the electrode to which a slightly negative potential was applied (see the lower portion of FIG. 2).

(2) The application of a high-frequency wave potential (±1.0 V vs. Ag/AgCl, 3 MHz rectangular wave) to the microorganisms (prokaryotes) that had attached to the electrode substrate resulted in the detachment and retrieval of 99 percent of the microorganisms from the electrode surface with almost no damage (middle portion of FIG. 2). The survival rate of the microorganisms remaining on the electrode surface one hour after application of the high-frequency wave potential was 91 percent (=517/566 cells). The retrieval rate of live bacteria from the soil was 84 percent (=154/183). Measurement by hemacytometer revealed that $3 \times 10^6$ microorganisms had been successfully retrieved from 50 micrograms of soil.

Example 2

(1) In the order indicated below, microorganisms were attached to and detached from ITO electrodes in the 3-electrode chamber shown in FIG. 1A, and a live/dead determination was made (see FIG. 1B).
1) *E. coli* or *B. subtilis* was cultured overnight in 5 mL of Luria-Bertani medium (LB medium, Difco Laboratories, Inc., Detroit, Mich., USA) at 37° C. and 120 rpm.
2) The medium was processed in a centrifuge, the supernatant was discarded, and the pellet was resuspended in 5 mL of Dulbecco's PBS(−).
3) A cell count was taken with a hemacytometer and the microorganisms were poured into a 3-electrode chamber at $1 \times 10^6$ cells/well.
4) A −0.4 V vs. Ag/AgCl potential was applied for 24 hours at room temperature.
5) After applying the potential for 24 hours, the supernatant was retrieved and the ITO pattern electrode substrate was washed lightly several times with fresh Dulbecco's PBS(−).
6) A 5 mL quantity of fresh Dulbecco's PBS(−) was added to the 3-electrode chamber and a ±1.0 V vs. Ag/AgCl, 3 MHz rectangular wave potential was applied for another one hour at room temperature.
7) Following application of the potential for one hour, the supernatant of the PBS(−) sample was retrieved and the ITO pattern electrode substrate was washed lightly several times with fresh Dulbecco's PBS(−).
8) The living microorganisms having dehydrogenase activity that had attached to the ITO electrodes in 5) were fluorescence stained with Bacstain CTC rapid staining kit for microscopy (Dojindo, Kumamoto, Japan) and then observed by confocal laser microscopy (FV500, Olympus, Tokyo, Japan).
9) The microorganisms that attached to the ITO electrodes in 5) and 7) were fluorescence stained with Live/dead Baclight bacterial viability kits (Molecular probes, Eugene, Oreg., USA) and a determination was made as to whether they were alive or dead by confocal laser microscopy (FV500).
10) A 100 μL quantity of the supernatant sample retrieved in 5) and 7) was poured onto an LB agar plate and the colonies were counted.

Figure 3:
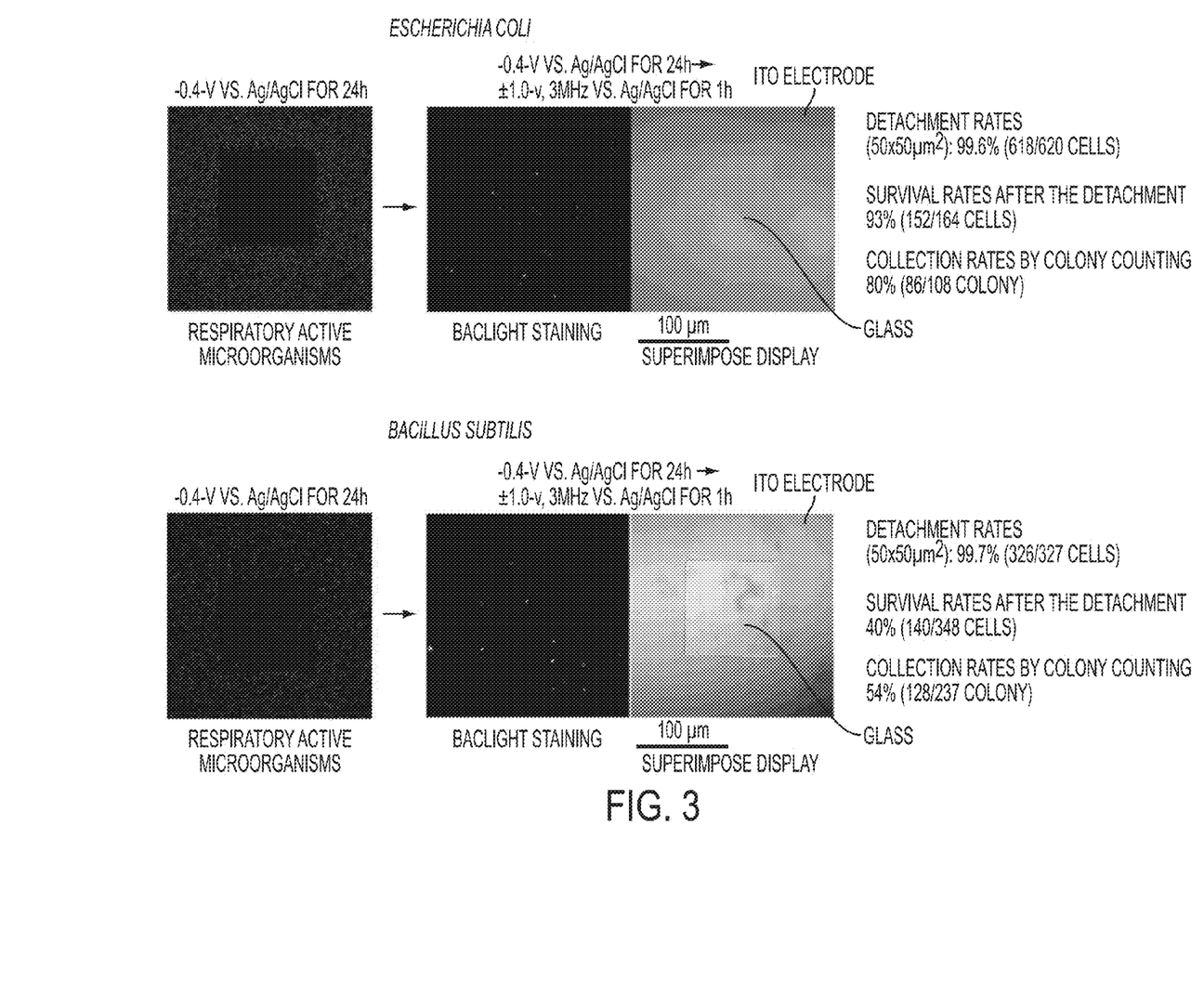
[FIG. 3] Shows result of attraction and attachment of *E. coli* and *B. subtilis* onto electrode and detachment and retrieval therefrom in Example 2.

The results are given in FIG. 3. The above electrical attachment was successful for both *E. coli*, a Gram-negative bacterium, and *B. subtilis*, a Gram-positive bacterium. The microorganisms that had been electrically attached were also successfully detached.

The survival rate of the microorganisms remaining on the electrode surface one hour after application of the high-frequency wave potential was 93 percent (=152/164 cells) for *E. coli* and 40 percent (=140/348 cells) for *B. subtilis*. The retrieval rate of live bacteria from the soil was 80 percent (=86/108 colonies) for *E. coli* and 54 percent (=128/237 colonies) for *B. subtilis*.

Example 3

In the following order and by the same method as in Example 1, the potential applied was varied and microorganisms in soil were caused to attach to the electrode surface.
1) A 0.5 g quantity of soil from a JAMSTEC vegetable garden in which no agricultural chemicals had been employed was added to Dulbecco's PBS(−) (Wako, Osaka, Japan), the overall quantity was adjusted to 5 mL, and the mixture was stirred for 5 minutes with a vortex.
2) The mixture was diluted $10^4$-fold with Dulbecco's PBS(−) and 10 ng/mL soil samples were prepared.
3) The 5 mL soil sample solution was added to a 3-electrode chamber and various constant potentials were applied at room temperature for 24 hours.
4) After applying the potential for 24 hours, the ITO pattern electrode substrate was washed lightly several times with fresh Dulbecco's PBS(−).
5) The living microorganisms having dehydrogenase activity that had attached to the ITO electrodes were fluorescence stained with a Bacstain CTC rapid staining kit for microscopy (Dojindo, Kumamoto, Japan) and then observed by confocal laser microscopy (FV500, Olympus, Tokyo, Japan).

Figure 4:
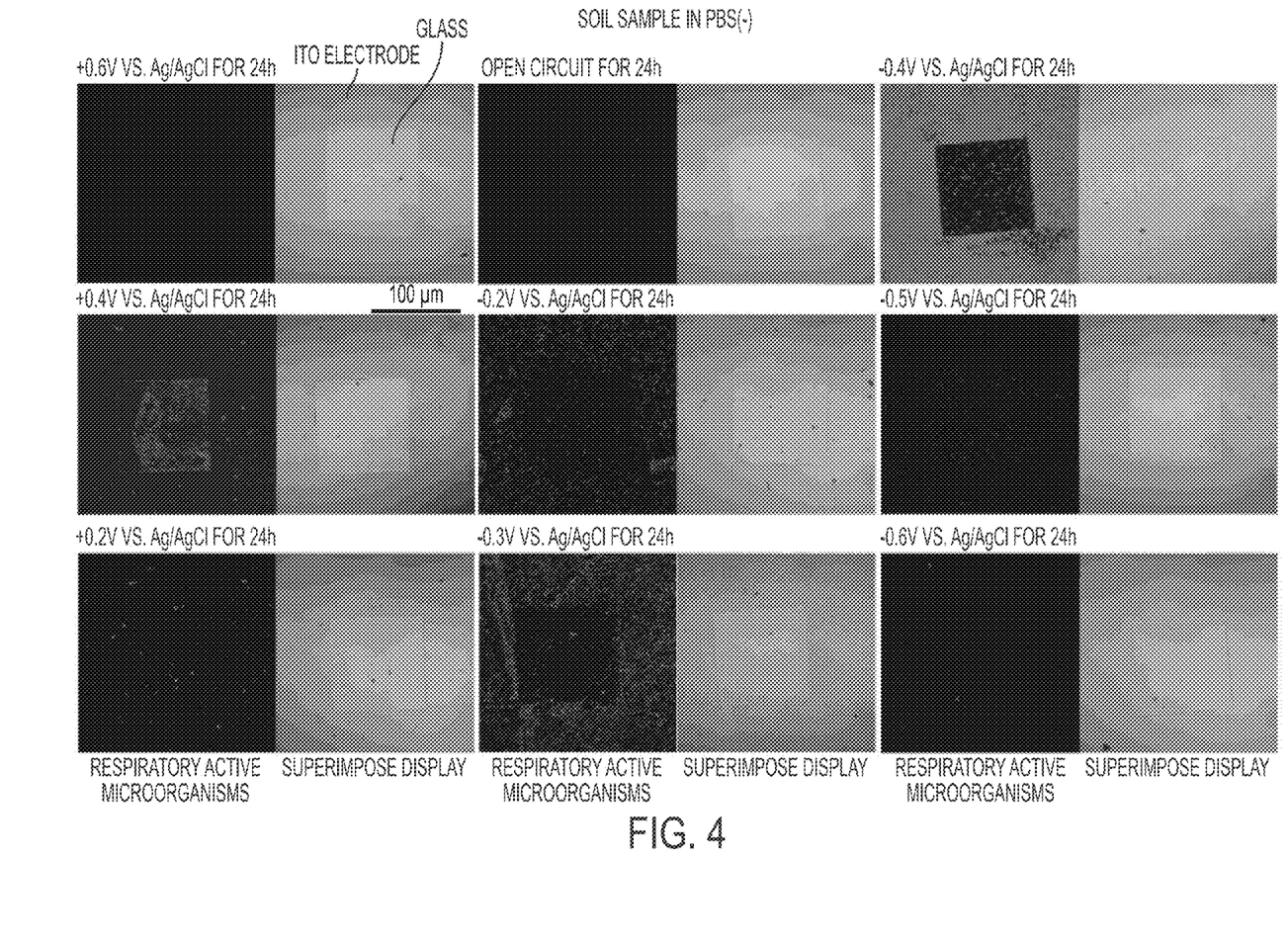
[FIG. 4] Shows the result of attraction and attachment of soil microorganisms onto electrode in Example 3.

The results are given in FIG. 4. The attachment to the electrode substrate of the microorganisms in soil was confirmed under conditions of the 24 hour application of constant potentials of −0.2 V, −0.3 V, −0.4 V, vs. Ag/AgCl. Some of the soil microorganisms were confirmed to be of a type that attached even at a constant potential of ±0.4 V applied for 24 hours.

Example 4

In the following order, microorganisms that had been caused to attach to the electrode surface by the same method as in Example 1 were detached from the electrode surface while varying the rectangular wave potential applied.
1) A 0.5 g quantity of soil from a JAMSTEC vegetable garden in which no agricultural chemicals had been employed was added to Dulbecco's PBS(−) (Wako, Osaka, Japan), the overall quantity was adjusted to 5 mL, and the mixture was stirred for 5 minutes with a vortex.
2) The mixture was diluted $10^4$-fold with Dulbecco's PBS(−) and 10 μg/mL soil samples were prepared.
3) The 5 mL soil sample solution was added to a 3-electrode chamber (see FIG. 1A) and a −0.4 V vs. Ag/AgCl potential was applied at room temperature for 24 hours.
4) After applying the potential for 24 hours, the ITO pattern electrode substrate was washed lightly several times with fresh Dulbecco's PBS(−).
5) A 5 mL quantity of fresh Dulbecco's PBS(−) was added to the 3-electrode chamber and ±0.4 V, ±0.8 V, ±1.0 V vs. Ag/AgCl, 3 MHz rectangular wave potentials were applied for another one hour at room temperature.
6) Following application of the potential for one hour, the ITO pattern electrode substrate was washed lightly several times with fresh Dulbecco's PBS(−).
7) The living microorganisms having dehydrogenase activity that had attached to the ITO electrodes in 4) were fluorescence stained with a Bacstain CTC rapid staining kit for microscopy (Dojindo, Kumamoto, Japan) and then observed by confocal laser microscopy (FV500, Olympus, Tokyo, Japan).
8) The microorganisms that had attached to the ITO electrodes in 6) were fluorescence stained with Live/dead Baclight bacterial viability kits (Molecular probes, Eugene, Oreg., USA) and a determination was made as to whether they were alive or dead by confocal laser microscopy (FV500).
9) The detachment rate was calculated from the quantity of microorganisms per $50 \times 50$ μm² that had attached to the ITO electrodes in 4) and 6).

Figure 5:
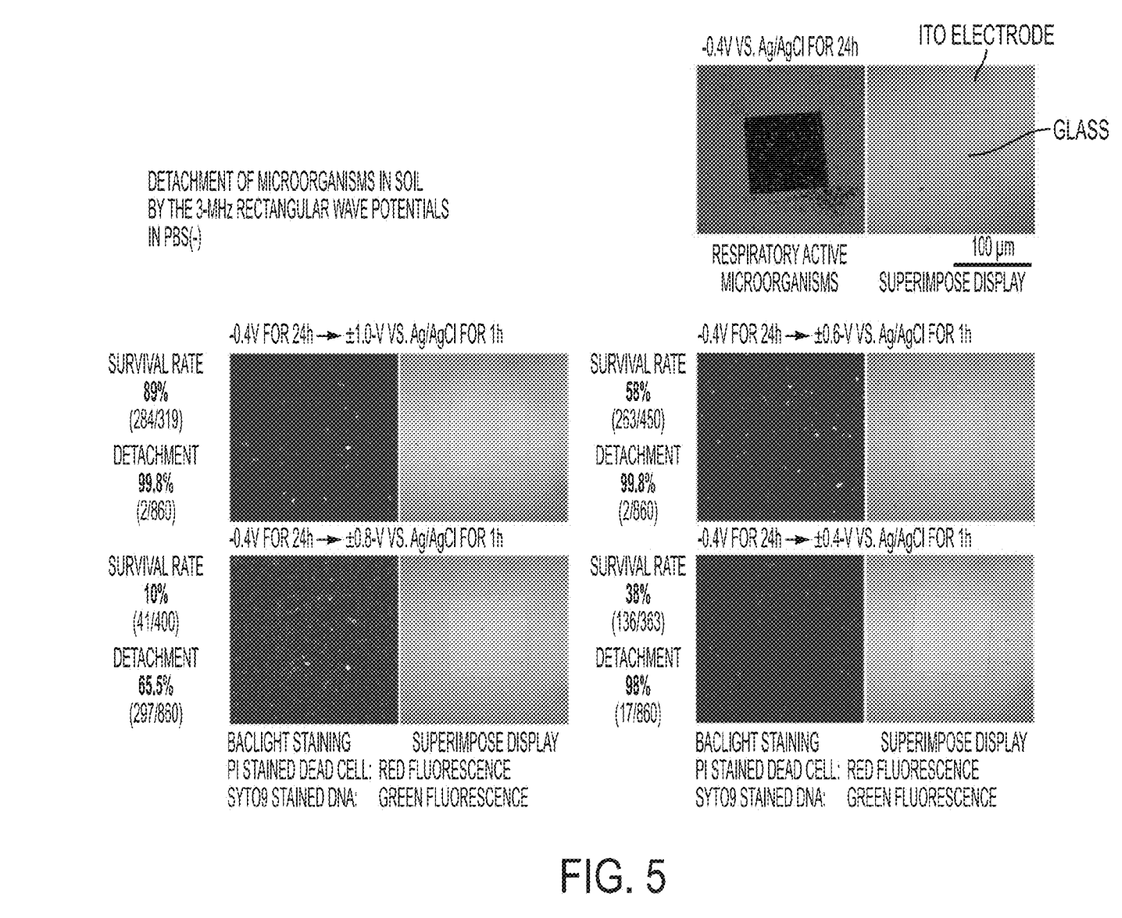
[FIG. 5] Shows the results of electrical detachment of soil microorganisms in Example 4.

The results are given in FIG. 5. The microorganism survival rates and the detachment rates from the electrode substrate when the various 3 MHz rectangular wave potentials had been applied for one hour are given. Detachment occurred at optimal conditions of a survival rate of 89 percent and a detachment rate of 99.8 percent at ±1.0 V.

Example 5

Figure 6:
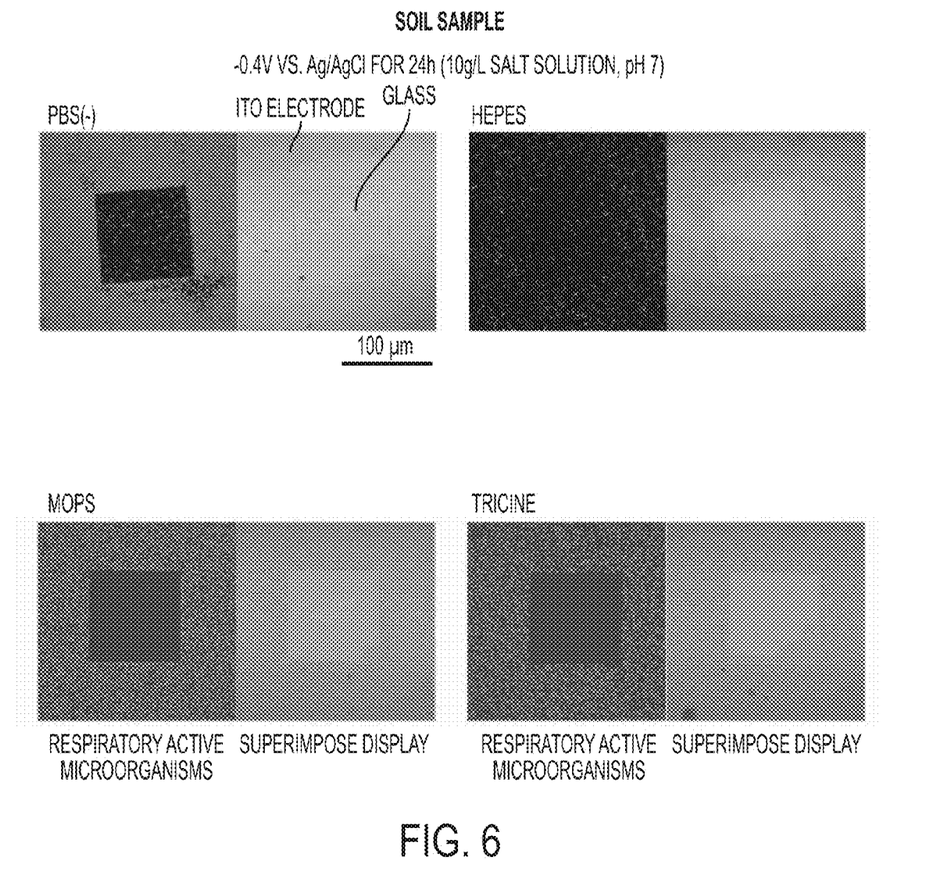
[FIG. 6] Shows the results of attraction and attachment of microorganisms in various buffers in Example 5.
Figure 7:
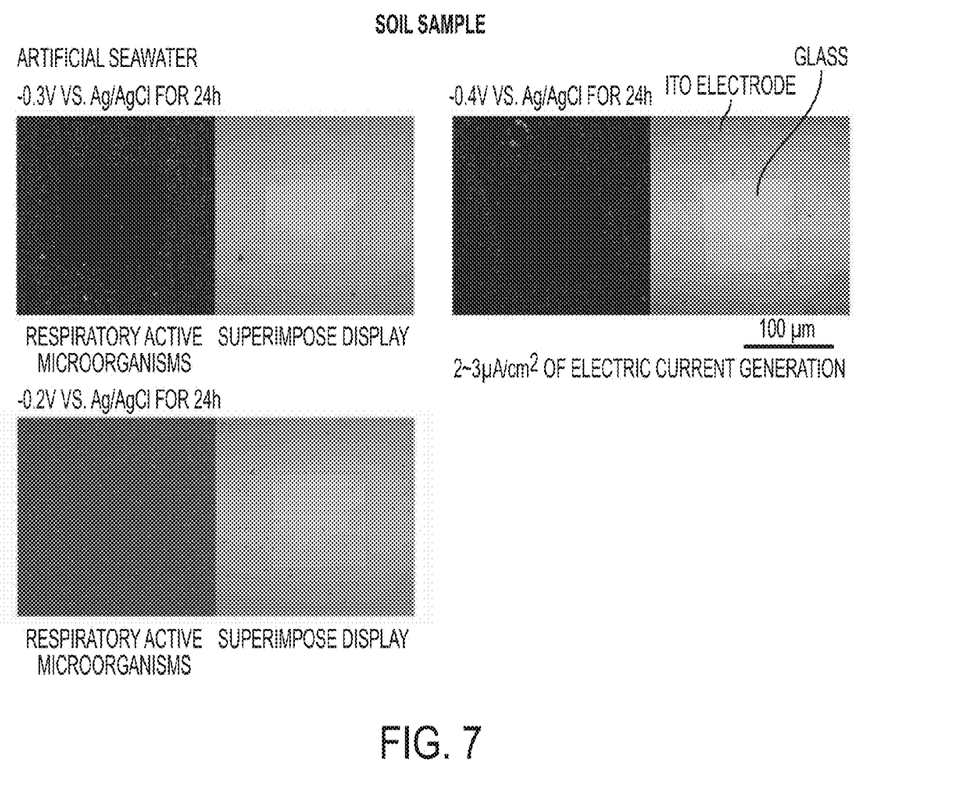
[FIG. 7] Shows the results of attraction and attachment of microorganisms in artificial seawater in Example 5.

In the following order, microorganisms in soil were caused to attach to the electrode surface by the same method as in Example 1 while varying the electrolyte employed.
1) 10 g/L of MOPS (Dojindo), Tricine (Dojindo), HEPES (cell culture tested, Sigma, St. Louis, Mo., USA) were adjusted to pH 7)
2) Artificial seawater (30 g/L NaCl, 0.7 g/L KCl, 5.3 g $MgSO_4\text{-}7H_2O$, 10.8 g $MgCl_2\text{-}6H_2O$, and 1.0 g/L $CaSO_4\text{-}2H_2O$ were prepared.
3) 0.5 g quantities of soil from a JAMSTEC vegetable garden in which no agricultural chemicals had been employed were added to the various buffers and artificial seawaters, the overall quantities were adjusted to 5 mL, and the mixtures were stirred for 5 minutes with a vortex.
4) The mixtures were diluted with the various buffers and seawaters to $10^4$-fold and 10 μg/mL soil samples were prepared.
5) 5 mL soil sample solutions were added to a 3-electrode chamber and various constant potentials were applied at room temperature for 24 hours.
6) After applying the potential for 24 hours, the ITO pattern electrode substrates were washed lightly several times with fresh Dulbecco's PBS(-).
7) The living microorganisms having dehydrogenase activity that had been attached to the ITO electrodes were fluorescence stained with Bacstain CTC rapid staining kit for microscopy (Dojindo, Kumamoto, Japan) and then observed by confocal laser microscopy (FV500, Olympus, Tokyo, Japan).
(1) The various buffers
The results are given in FIG. 6. An attempt was made to electrically adsorb the microorganisms in soil in 10 g/L of various buffers by 24 hours at -0.4 V vs. Ag/AgCl. As a result, PBS(-) exhibited the best electric adsorption, followed by MOPS buffer and Tricine buffer. HEPES somewhat blocked the adsorption of the microorganisms on the electrodes.
(2) The artificial seawaters
The results are given in FIG. 7. Between -0.3 V and +0.6 V vs. Ag/AgCl, no current flowed in the artificial seawaters, so no pattern could be confirmed for the adsorbed microorganisms. The optimal conditions for electric adsorption of microorganisms in artificial seawater was -0.3 V vs. Ag/AgCl.

Comparative Example 1

In the order given below, soil microorganisms for which the electrolyte employed was replaced with medium (containing sources of nutrition) were caused to attach to the electrode surface by the same method as in Example 1. An examination of whether soil microorganisms would attach to the electrode substrate even in medium was conducted.
1) A 0.5 g quantity of soil from a JAMSTEC vegetable garden in which no agricultural chemicals had been employed was added to Dulbecco's PBS(-) (Wako, Osaka, Japan), the overall quantity was adjusted to 5 mL, and the mixture was stirred for 5 minutes with a vortex.
2) The mixture was diluted $10^4$-fold with Luria-Bertani medium (LB medium, Difco Laboratories, Inc., Detroit, Mich., USA) and 10 μg/mL soil samples were prepared.
3) The 5 mL soil sample solutions were added to a 3-electrode chamber and a -0.4 V vs. Ag/AgCl potential was applied at room temperature for 24 hours.
4) After applying the potential for 24 hours, the ITO pattern electrode substrate was washed lightly several times with fresh Dulbecco's PBS(-).
5) The microorganisms that had attached to the ITO electrodes were fluorescence stained with Live/dead Baclight bacterial viability kits (Molecular probes, Eugene, Oreg., USA) and observed by confocal laser microscopy (FV500).

Figure 8:
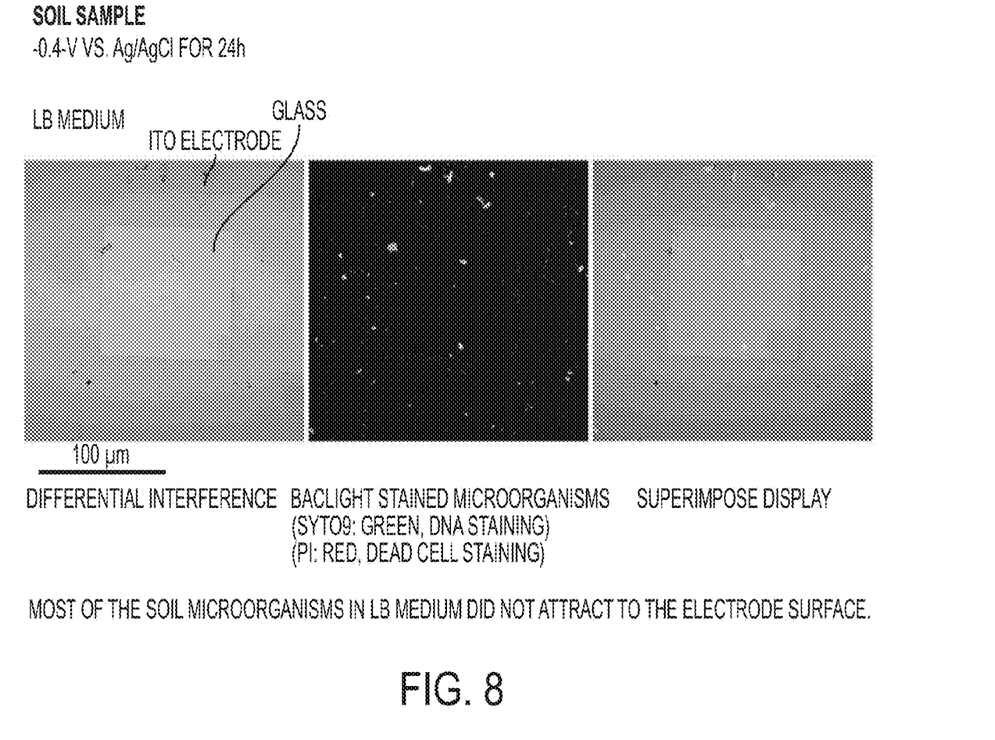
[FIG. 8] Shows the results of attracting microorganisms in medium onto an electrode in Comparative Example 1.

The results are given in FIG. 8. The soil microorganisms were not attracted and did not attach to the electrode substrate.

Comparative Example 2-1

In the order given below, soil microorganisms for which the electrolyte employed was replaced with a mannitol solution were caused to attach to the electrode surface by the same method as in Example 1.
1) A 0.5 g quantity of soil from a JAMSTEC vegetable garden in which no agricultural chemicals had been employed was added to Dulbecco's PBS(-) (Wako, Osaka, Japan), the overall quantity was adjusted to 5 mL, and the mixture was stirred for 5 minutes with a vortex.
2) The mixture was diluted $10^4$-fold with a 280 mM mannitol aqueous solution and a 10 μg/mL soil sample was prepared.
3) The 5 mL soil sample solution was added to a 3-electrode chamber and a -0.4 V vs. Ag/AgCl potential was applied at room temperature for 24 hours.
4) After applying the potential for 24 hours, the ITO pattern electrode substrate was washed lightly several times with fresh Dulbecco's PBS(-).
5) The microorganisms that had attached to the ITO electrode were fluorescence stained with Live/dead Baclight bacterial viability kits (Molecular probes, Eugene, Oreg., USA) and observed by confocal laser microscopy (FV500).

Figure 9:
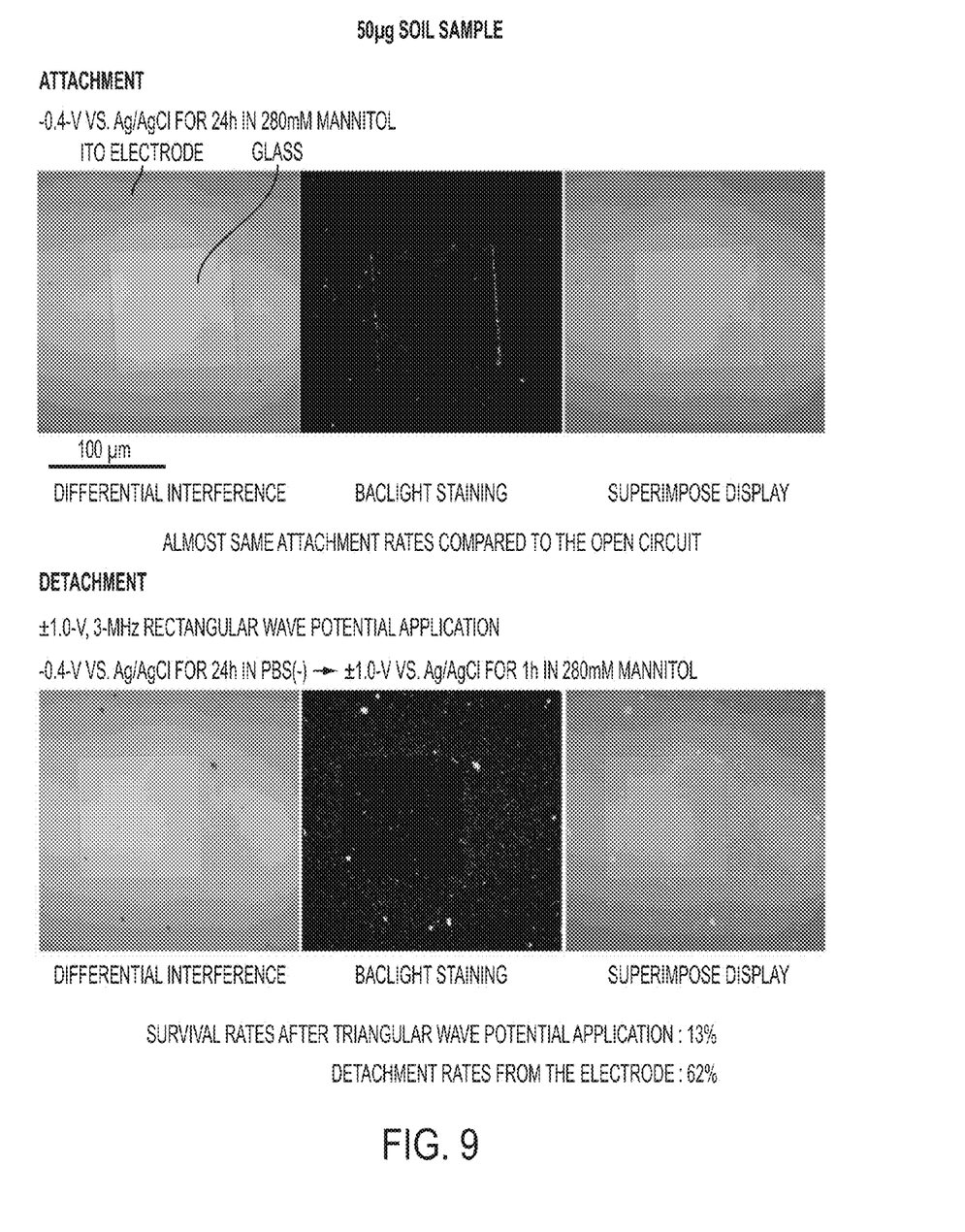
[FIG. 9] Shows the results of attracting microorganisms in 280 mM mannitol aqueous solution onto an electrode in Comparative Example 2.

The results are given in the top portion of FIG. 9. In the 280 mM mannitol aqueous solution, under the conditions of the present invention, the microorganisms did not attach to the same degree as when no voltage was applied (open circuit).

Comparative Example 2-2

In the order given below, soil microorganisms for which the electrolyte employed was replaced with a mannitol solution were caused to attach to the electrode surface by the same method as in Example 1, and then detached in a mannitol solution.
1) A 0.5 g quantity of soil from a JAMSTEC vegetable garden in which no agricultural chemicals had been employed was added to Dulbecco's PBS(-) (Wako, Osaka, Japan), the overall quantity was adjusted to 5 mL, and the mixture was stirred for 5 minutes with a vortex.
2) The mixture was diluted $10^4$-fold with Dulbecco's PBS(-) and 10 μg/mL soil samples were prepared.
3) The 5 mL soil sample solution was added to a 3-electrode chamber and a -0.4 V vs. Ag/AgCl potential was applied at room temperature for 24 hours.
4) After applying the potential for 24 hours, the ITO pattern electrode substrate was washed lightly several times with fresh Dulbecco's PBS(-).
5) A 5 mL quantity of a 280 mM mannitol aqueous solution was added to a 3-electrode chamber and a ±1.0 V vs. Ag/AgCl, 3 MHz rectangular wave potential as applied for another one hour at room temperature.
6) Following application of the potential for one hour, the ITO pattern electrode substrate was washed lightly several times with fresh Dulbecco's PBS(-).

7) The microorganisms that had attached to the ITO electrodes were fluorescence stained with Live/dead Baclight bacterial viability kits (Molecular probes, Eugene, Oreg., USA) and a determination was made as to whether they were alive or dead by confocal laser microscopy (FV500).

The results are given in the lower portion of FIG. 9. Almost none of the attached microorganisms detached under the conditions of the high-frequency potential applied in the present invention, and almost all ended up dying.

INDUSTRIAL APPLICABILITY

The present invention is useful in the field of handling microorganisms.

The invention claimed is:

1. A method for immobilizing living prokaryotic microorganisms comprising a step (1) of disposing a solution, which contains microorganisms, as an electrolyte on the surface of a substrate at least one portion of which is an electrode, and applying a constant potential to the electrode to cause at least a portion of the microorganisms to attach to the surface of the substrate, wherein
the constant potential in step (1) is greater than −0.5 V but not greater than −0.2 V (vs Ag/AgCl); and
the electrolyte in step (1) does not contain a source of nutrition for the microorganisms.

2. A method for preparing living prokaryotic microorganisms, comprising a step (1) of disposing a solution, which contains microorganisms, as an electrolyte on the surface of a substrate at least one portion of which is an electrode, applying a constant potential to the electrode to cause at least a portion of the microorganisms to attach to the surface of the substrate and a step (2) of applying a high-frequency wave potential to the electrode to detach in a viable condition the microorganisms that have been attached to the surface of the substrate; wherein
the constant potential in step (1) is greater than −0.5 V but not greater than −0.2 V (vs Ag/AgCl);
the high-frequency wave potential in step (2) has a frequency falling within a range of 1KHz to 10 MHz and a potential range of ±1.0 V (vs Ag/AgCl) or narrower;
the electrolyte in step (1) does not contain a source of nutrition for the microorganisms; and
the electrolyte of step (2)) has a salt concentration of 10 g/L or lower.

3. The method according to claim 1 or 2, wherein the electrolyte in step (1) has a salt concentration of 10 g/L or lower.

4. The method according to claim 1 or 2, wherein the electrolyte in steps (1) and (2) is $Ca^{2+}$ and $Mg^{2+}$ free phosphate buffer solution.

5. The method according to claim 1 or 2, wherein the electrolyte in step (1) is artificial seawater or natural seawater, and the constant potential in step (1) is greater than −0.4 V but not greater than −0.2 V (vs Ag/AgCl).

6. The method according to claim 1 or 2, wherein the entire surface of the substrate is an electrode.

7. The method according to claim 2, wherein the high-frequency wave potential is a rectangular wave, sine wave, or triangle wave.

8. The preparation method according to claim 2, wherein a portion of the surface of the substrate is an electrode, and the microorganisms on the electrode surface and on the non-electrode surface in the vicinity of the electrode in step (2) are detached in a viable condition.

9. The preparation method according to claim 2, comprising the step of further cultivating the microorganisms that have been detached to cause the microorganism to proliferate.

* * * * *